United States Patent [19]

Quivy et al.

[11] Patent Number: 5,096,694

[45] Date of Patent: * Mar. 17, 1992

[54] COMPOUNDS WHICH ARE USEFUL, IN PARTICULAR, FOR RADIOTHERAPY OR IMAGING OF CANCER

[75] Inventors: Jacques Quivy, Ottignies/Louvain-la-Neuve; Marc Zeicher, Brussels, both of Belgium; Manuel Worcel, Paris, France

[73] Assignee: Ire-Celltarg S.A., Belgium

[*] Notice: The portion of the term of this patent subsequent to Mar. 26, 2008 has been disclaimed.

[21] Appl. No.: 297,864

[22] PCT Filed: Apr. 19, 1988

[86] PCT No.: PCT/FR88/00188

§ 371 Date: Dec. 15, 1988

§ 102(e) Date: Dec. 15, 1988

[87] PCT Pub. No.: WO88/07986

PCT Pub. Date: Oct. 20, 1988

[30] Foreign Application Priority Data

Apr. 17, 1987 [FR] France .................. 87 05524

[51] Int. Cl.$^5$ .................. A61K 43/00; A61K 49/02
[52] U.S. Cl. .................. 424/1.1; 436/504
[58] Field of Search .................. 424/1.1; 436/504

[56] References Cited

U.S. PATENT DOCUMENTS

| 4,465,676 | 8/1984 | Hochberg .................. 424/1.1 X |
| 4,541,957 | 9/1985 | Nakatsuka et al. .................. 424/1.1 X |
| 4,725,426 | 2/1988 | Hofmeister et al. .................. 424/1.1 |
| 4,882,141 | 11/1989 | Baranczuk et al. .................. 424/1.1 |
| 4,945,064 | 7/1990 | Hofmeister et al. .................. 424/1.1 X |
| 5,002,753 | 3/1991 | Zeicher et al. .................. 424/1.1 |

FOREIGN PATENT DOCUMENTS 169515 1/1986 European Pat. Off. .
518547 11/1975 Fed. Rep. of Germany .

OTHER PUBLICATIONS v.d. Broek et al., *Recueil, Journal of the Royal Netherlands Chemical Society,* (1975) 92(2):35-39.
De Flines et al., *Recueil* (1963) 82:129-139.
Brown and Coleman in *J. Org. Chem.* (1979) 44(13):2328-2329.
Nakatsuka et al., *J. Med. Chem.* (1984) 27:1287-1291.
v.d. Broek et al., *Steroids* (1977) 30(4):481-510.
Corey and Suggs in *Tetrahedron Letters* (1975) 31:2647-2650.
Schonemann et al., in *Eur. J. Med. Chem.—Chemica Therapeutica* (1980) 15(4):333-335.
v.d. Broek et al. in *Pharmaceutisch Weekblad Scientific Edition* (1983) 5:182-183.
Hanson et al., *The Journal of Nuclear Medicine* (1982) 23:431-436.
Smith et al., *Journal of Medicinal Chemistry* (1979) 22(1):40-44.
Tong et al., *Journal of Medicinal Chemistry* (1976) 19(3):395-398.
Glamkowski et al., *Journal of Medicinal Chemistry* (1979) 22(1):106-109.
L. A. Franke et al., Radioiodinated Ligands for the Estrogen Receptor: Effect of 3-o-Methylation on Tissue Distribution, *J. of Nuclear Medicine,* (1984) 25:1116-1121.
T. Ratajczak et al., The Synthesis and Study of Some Potential Affinity Labeling Reagents for Estrogen Receptors, *Steroids,* (1981) 38:537-555.

*Primary Examiner*—Richard D. Lovering
*Assistant Examiner*—John M. Covert
*Attorney, Agent, or Firm*—Cooley, Godward, Castro, Huddleson & Tatum

[57] ABSTRACT

Compound useful particularly for the treatment by targetted radiotherapy or imaging of cancer, characterized in that the compound is comprised of a molecule susceptible of fixing itself or passing close to the DNA of the target cells, said molecule being radiolabelled with iodine 123. The invention also relates to new ligands specific of steroid hormone receivers useful for the targetted therapy or imaging particularly of cancer and presenting a structural base skeleton having the formula (I). According to the invention these ligands comprise particularly a) a hydroxyl or ketone function in position $C_3$; b) a $\beta$ chloromethyl function on position $C_{11}$; c) an $\alpha$ methyl or vinyl function on position $C_{17}$ and d) a substituted radioactive iodine on an alkyl or alkenyl group attached to the skeleton, particularly methyl or vinyl.

20 Claims, No Drawings

COMPOUNDS WHICH ARE USEFUL, IN PARTICULAR, FOR RADIOTHERAPY OR IMAGING OF CANCER

The technical field of the present invention is that of targeted therapy and of medical imaging, in particular of cancer.

The present invention relates especially to the treatment of disseminated cancers using targeted cytotoxic radioisotopes.

According to the invention, the target for the ionizing radiation administered is the DNA of malignant cells. The sterilizing effect of the radiation is due predominantly to the induction of double breaks in the DNA.

The use of radioisotopes which disintegrate emitting Auger electrons is very opportune for this purpose. Due to the short range of AUGER electrons, the efficacy of such radioisotopes in relation to cellular inactivity is completely lost when they are not linked to, or at the very most at a distance of a few atoms from, the DNA.

In contrast, such radioisotopes become very effective when they are linked to molecules that are incorporated in DNA or that bind to DNA.

$^{125}$I and $^{80m}$Br have already been proposed for this purpose. However, $^{125}$I is not ideal for this application in vivo in view of its half-life of 60 days.

For example, the turnover of estrogen/estrogen receptor complexes takes place on a scale measured in hours and not in days, which means that only a small fraction of the radioactivity administered to the patient will reach the target cells at the appropriate time, and that the patient will be exposed needlessly to a large amount of radioactivity.

Bromine-$80^m$, on the other hand, has a half-life of 4.4 hours, which makes it obligatory in practice to treat the patient in the immediate vicinity of the cyclotron. In addition, Br-$80^m$ produces only an average of 6 to 7 AUGER electrons per disintegration.

It has been discovered, according to the invention, that iodine-123, which has a half-life of 13.21 hours and produces about twenty AUGER electrons per disintegration, does not have the drawbacks of iodine-125 and of bromine-$80^m$. Its half-life is sufficiently short for the patient not to be exposed needlessly to doses of radioactivity during an extended period, but is sufficiently long to enable radiopharmaceutical products to be synthesized and dispatched to treatment centers located far from the production cyclotron, taking into account the fact that up to 48 hours' journey time and 24 hours of treatment must be anticipated.

In effect, the maximum specific activities for one radioactive halogen atom incorporated per molecule are as follows:

| | | |
|---|---|---|
| for Br-$80^m$ | 0 h | 712,415 Ci/mmol |
| $N_{24h} = N_o \times \frac{1}{43.816}$ | 24 h | 16,259 Ci/mmol |
| | 48 h | 371 Ci/mmol |
| | 72 h | 8 Ci/mmol |
| for I$^{123}$ | 0 h | 237,292 Ci/mmol |
| $N_{24h} = N_o \times \frac{1}{3.522}$ | 24 h | 67,373 Ci/mmol |
| | 48 h | 19,129 Ci/mmol |
| | 72 h | 5,431 Ci/mmol |
| for I$^{125}$ | 0 h | 2,177 Ci/mmol |
| $N_{24h} = N_o \times \frac{1}{1.0116}$ | 24 h | 2,152 Ci/mmol |
| | 48 h | 2,127 Ci/mmol |
| | 72 h | 2,103 Ci/mmol |

Ci (curie)

In addition, the activity decreases very rapidly after 72 hours for I$^{123}$, whereas it persists with I$^{125}$, allowing needless contamination.

Thus, the subject of the present invention is a compound which is useful, in particular, for the treatment by targeted radiotherapy or the imaging of cancer, which compound consists of a molecule capable of binding to or passing close to the DNA of target cells, the said molecule being radiolabeled with iodine-123.

As a molecule capable of binding to or passing close to the DNA of target cells, there may be mentioned nucleoside analogs, the nucleoside being substituted on its base with a radionuclide that emits I$^{123}$ AUGER electrons, corresponding to the formula

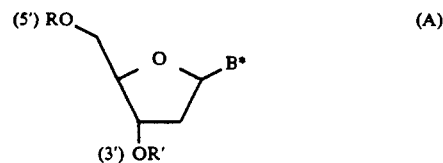

in which

B* denotes one of the substituted bases adenine, thymine, guanine, cytosine or uracil, labeled with a radionuclide that emits I$^{123}$ AUGER electrons R and R' denote H or a protective group such as acetyl or benzoyl.

Nucleoside analog is hence understood to mean a substance having the structure of a natural nucleoside but in which the base of the sugar portion can have an unnatural substitution.

These small-sized substances can enter the cell through its membrane and be introduced right into the DNA helix as the result of the affinity of each nucleoside analog present for a nucleoside in which the base is complementary.

In particular, there may be mentioned the compound which is a thymidine analog of formula

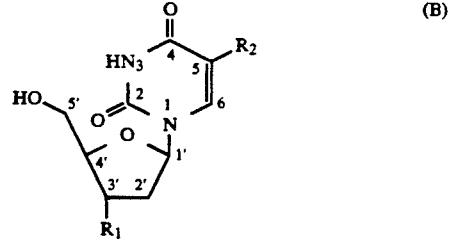

in which $R_1$ denotes H, OH, $N_3$ or OR; where R is as defined for the formula (A)

$R_2$ denotes I$^{123}$, $CH_2I^{123}$ or $CH=CHI^{123}$.

For example, the nucleoside analog is 5-iodo-2'-deoxyuridine ($R_1$=OH and $R_2$=I$^{123}$).

Intercalating agents, which are known compounds in the arts relating to nucleic acids, capable of intercalating in the DNA or RNA structure, may also be mentioned as compounds according to the invention.

These substances having an affinity with DNA or intercalating in its structure are hence especially suitable for carrying radionuclides close to DNA when they have been labeled with these radionuclides.

Intercalating agents are polycyclic compounds having a flat configuration, such as acridine, furocoumarin, 1,10-phenanthroline, phenanthridine, porphyrins, ellipticine, psolaren, anthracyclines such as daunorubicin or doxorubicin or their derivatives, actinomycin, echinomycin, nogalamycin, netropsine, berenil or their analogs.

Daunorubicin analogs and doxorubicin analogs iodinated on their side chain at C9 may be mentioned in particular.

Among these derivatives, there may be mentioned those which correspond to the following formula:

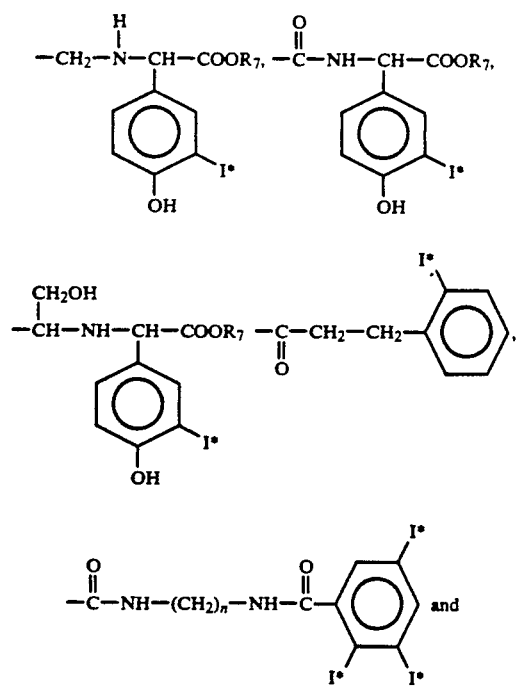

(C)

in which,

—R6 is chosen from the monovalent residues

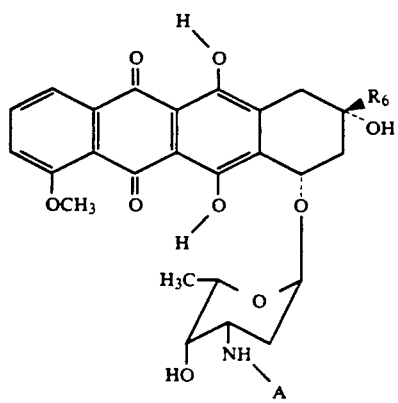

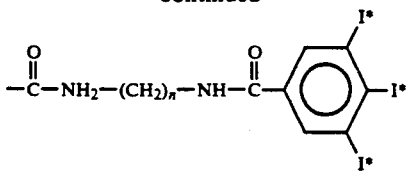

-continued

A is H or a chain of peptide nature represented, in particular, by X'-L Leu where L Leu denotes an L-leucyl residue linked via its carboxyl group to the amine group of anthracycline and X' denotes 1, 2 or 3 identical or different amino acids.

Ligands specific for steroid hormone receptors may also be mentioned as molecules capable of passing close to the DNA of target cells.

Steroid hormones bind with high affinity to the cytoplasmic protein receptors of target cells and, after binding, undergo a translocation to the cell nucleus and activate the transcription of the portions of the genome relating to the physiological effect specific to the hormone. In view of the passage of the steroid/receptor complex close to the DNA, a radioactive iodine $I^{125}$ or $I^{123}$ borne by the steroid may severely damage the DNA and have a lethal effect on the target cell.

Now, a number of cancers show a high concentration of receptors specific either for estrogens, or for progestagens or for androgens. This is the case, in particular, with cancers of the breast, the uterus, the ovary and the prostate. For example, 65% of breast cancers show detectable levels of estrogen receptors (from 5000 to 50,000 receptor molecules per cell).

A radioactive iodine $I^{125}$ or $I^{123}$ attached to the steroid will enable the cancer cells to be specifically destroyed. In addition, an iodine-123 will enable the tumor to be visualized by radioimaging. In fact, these ligands constitute targeting agents for the actual active component, which is their radionuclide.

For intracellular binding sites such as hormone receptors, hormone analogs showing a high affinity for the receptor and a low affinity for plasma binding proteins will be the most suitable targeting agents.

In particular, there may be mentioned as compounds according to the invention all known ligands specific for steroid hormone receptors, such as 17betaiodovinylestradiol or 17beta-iodovinylnorethindrone or alternatively tamoxifen or hydroxytamoxifen which, according to the invention, bear an iodine-123 as radionuclide.

The present invention also relates to new steroid ligands specific for hormone receptors, which ligands can then bear a radionuclide $I^{125}$ or $I^{123}$.

An object of the present invention was also, in effect, to propose new analogs of steroid hormones showing a high affinity for the hormone receptor and which binds virtually irreversibly to the receptor with a view to improving the proportion of analogs bound, the iodo derivatives of these analogs having to be stable in the extracellular medium, in particular in the plasma, as well as in the cytoplasm, while retaining a high affinity for the hormone receptor.

All cells containing hormone receptors, whether malignant or healthy, may be subjected to this increase in cytotoxicity.

However, an improved selectivity is nevertheless observed since, in conventional cancer chemotherapeutic treatments, the healthy estrogenic target tissues either have a rate of cell proliferation which is low, or is not essential to life. The same applies to androgen and progestagen receptors.

The subject of the present invention is hence also new ligands specific for steroid hormone receptors, which are useful for the targeted therapy or the imaging, in particular of cancer, possessing a parent structural skeleton of the formula:

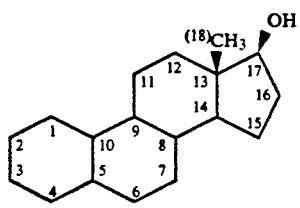

These products of formula I contain, in particular:
a a hydroxyl or keto group at the $C_3$-position,
b a $\beta$-oriented chloromethyl group on the $C_{11}$-position,
c an $\alpha$-oriented vinyl or methyl group on the $C_{17}$-position, and
d a radioactive iodine substituted on an alkyl or alkenyl group attached to the skeleton, in particular a methyl or a vinyl.

The groups at the $C_3$- and $C_{17}$-positions endow these ligands with a high affinity for the hormone receptors for which they are intended, namely androgen, estrogen or progestagen receptors, in particular.

The 11$\beta$-chloromethyl group provides for virtually "irreversible" binding between the steroid and the receptor; this binding, in fact, represents, more exactly, very strong affinity for the receptor.

The formation of the virtually "irreversible" link between the steroid and the receptor improves the stability of the complex and increases its concentration in the nucleus.

The binding sites of estrogen, androgen and progestagen hormones exhibit amino acid sequence homologies, which explains their common behavior as regards the "irreversible" binding between the receptor and the steroid in the presence of an 11$\beta$-chloromethyl group.

These derivatives possess a vinyl or methyl group at $C_{17}$ in the $\alpha$-orientation of the $C_{17}$-position, which endows them with a resistance to metabolism and a reduced binding to plasma binding protein.

The ligands which are more especially useful for targeted therapy will contain the isotope $I^{125}$ or $I^{123}$ as radioactive iodine.

This radioactive iodine thus targeted shows a strong cytotoxic activity, inasmuch as it is brought close to the DNA, in which it induces cleavages in the double helix.

Ligands which are more especially useful for medical imaging, in particular of cancer, will contain the isotope $I^{123}$ as radioactive iodine.

According to a first variant of the ligands according to the invention, the radioactive iodine is situated on the double bond of the $\alpha$-oriented vinyl on the $C_{17}$-position. These ligands are more specific for estrogen and progestagen receptors. This position has the advantage of showing great stability.

According to a second variant of the ligands according to the invention, the radioactive iodine is situated on an angular methyl position at $C_{18}$. The $C_{18}$- position is that which is directly linked to $C_{13}$. These ligands are more especially specific for androgen receptors.

As ligands according to the first variant, those in which the group at $C_3$ is a hydroxyl group, the ring to which it is attached being an aromatic ring, may be mentioned in particular. These ligands are more specific for estrogen receptors.

As ligands according to the first variant of the invention, ligands in which the group at the $C_3$-position is a keto group conjugated with a $C_4$-$C_5$ double bond may also be mentioned. These ligands are more especially specific for progestagen receptors.

Among the ligands which are more especially specific for androgen receptors, in which the radioactive iodine is situated on an angular methyl positioned at $C_{18}$, those in which the group at the $C_3$-position is a keto group conjugated with $C_4$-$C_5$ double bond may be mentioned.

Among the latter, those which contain a methyl at the $C_7$-position may also be mentioned.

Among ligands which are more specific for the estrogen receptors noted above, there may be mentioned 11$\beta$-chloromethyl-17$\alpha$-iodovinylestradiol of formula

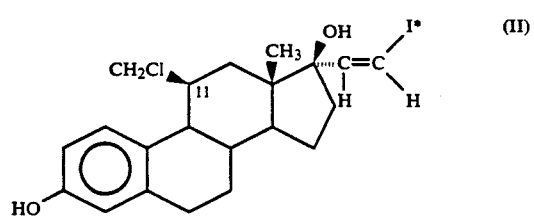

Among the most specific ligands for progestagen receptors, special mention may be made of 11$\beta$-chloromethyl-17$\alpha$-iodovinyl-17$\beta$-hydroxy-19-nor-4-androsten -3-one of formula

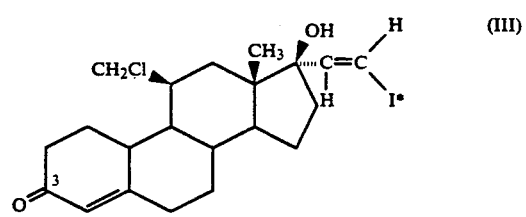

among specific ligands for androgen receptors, there may be mentioned 11$\beta$-chloromethyl-17$\alpha$-methyl-18-iodotestosterone or -19-nortestosterone of formula

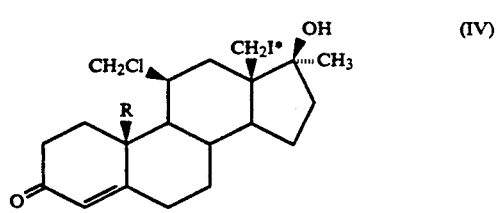

depending on whether R=CH$_3$ (testosterone derivative) or H (19-nortestosterone derivative)

Among these latter, there may also be mentioned 11$\beta$-chloromethyl-17$\alpha$-methyl-18-iodo-7$\alpha$-methyltestosterone or -19-nortestosterone of formula

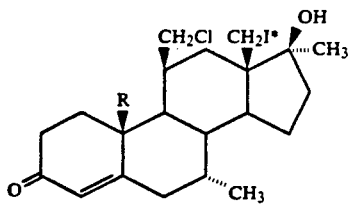

(V)

depending on whether R=CH₃ (testosterone derivative) or H (19-nortestosterone derivative)

Other features and advantages of the present invention will become apparent in the light of the description which follows.

EXAMPLE I

Nucleoside analog compounds

The compounds are represented by the following formula:

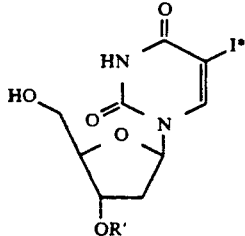

(A')

R and R'=H or a protective group, for example acetyl or benzoyl.

The various nucleoside analogs have been described. However, more especially, 5-iodo-2'-deoxyuridine, derived from commercially available nucleosides, has been synthesized by LIN T.S. and PRUSOFF, N.H. (J. med. Chem. 21, 106, 1978) ($R_1$=OH, $R_2$=I).

Naturally, the process encompasses any 5-halo(Cl, Br, I) derivative, since the synthesis of the radiolabeled derivative includes a stage of exchange of the halogen with $I^{123}$. This exchange is also possible using 5-chloro, 5-bromo or 5-iodo derivatives.

EXAMPLE II

Preparation of radioactive iodo derivatives of anthracyclines.

Synthesis of radioactive iodo derivatives of anthracyclines is carried out by ion exchange using nonradioactive iodo compounds.

The iodination of daunorubicin (DNR) derivatives and doxorubicin (DOX) derivatives is carried out on the side chain at $C_9$, according to several synthetic routes with the introduction either of a single iodine atom (A.) or of 3 iodine atoms (B.).

The anthracyclines are of the formula

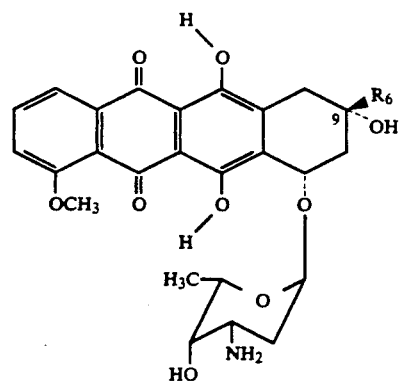

(C)

with
$R_6=$

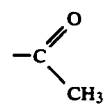

for daunorubicin and
$R_6=$

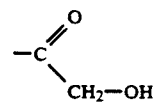

for doxorubicin.

The side group of the anthracycline at $C_9$ may be converted to a 9-formyl or 9-carboxyl derivative, which can be reacted with an iodinated aromatic amine.

I) From the 9-formylanthracycline.

The formation of the 9-formyl derivative of doxorubicin has been described by Smith et al. (J. Med. Chem. 22 (1979), 40-44), by a reduction with cyanoborohydride and oxidation of the enol with periodate. The reaction of 9-formyl-dox with iodotyrosine methyl ester leads to the Schiff's base which, after reduction with cyanoborohydride, gives a more stable compound.

The formula (C') below

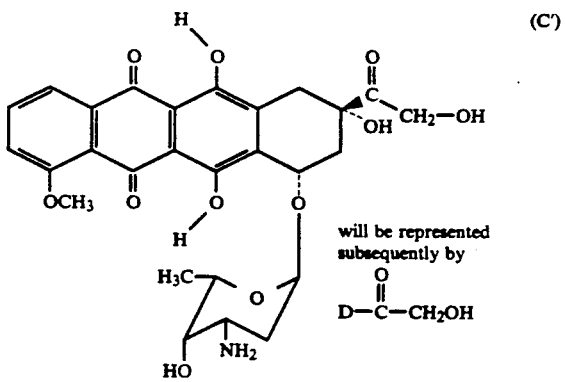

(C')

will be represented subsequently by

D—C̈—CH₂OH

1) The reaction of 9-formyldoxorubicin with iodotyrosine methyl ester leads to the Schiff's base which, after reduction with cyanoborohydride, gives a more stable compound, according to the scheme below:

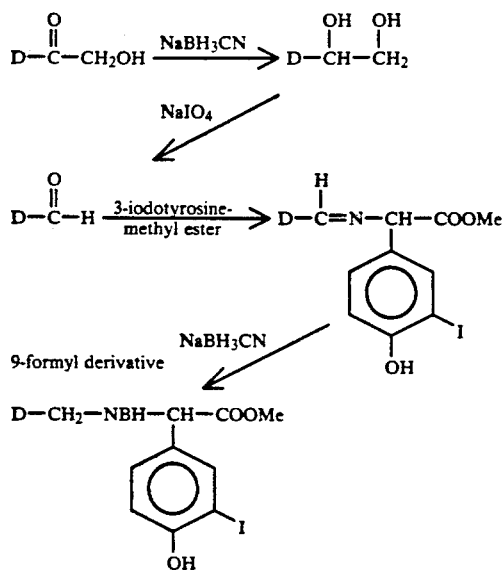

The exchange of the "cold" halogen with iodine-125 or -0123 is then performed. An alternative consists in reacting L-tyrosine methyl ester with the 9-formyl derivative and iodinating directly with iodine-125 or -123.

2) 9-Formyldoxorubicin is formed from doxorubicin. The latter reacts with either tyrosine methyl ester or 3-iodotyrosine methyl ester, as described in (1).

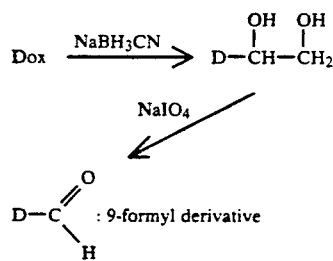

The 9-formyl derivative reacts with tyrosine methyl ester, is reduced with sodium cyanoborohydride and then iodinated with iodine-125 or -123.

According to the invention, an alternative is to react the 9-formyl derivative with 3-iodotyrosine methyl ester, then to reduce the Schiff's base with sodium cyanoborohydride and to perform "cold" iodine/I* exchange. The radioactive iodo derivative is then activated and coupled with its carrier protein.

II) From the anthracycline

The reaction between doxorubicin and tyrosine methyl ester or 3-iodotyrosine methyl ester is also possible, although slower than using the 9-formyl derivatives.

The reaction may be outlined in the following manner:

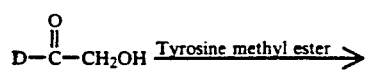

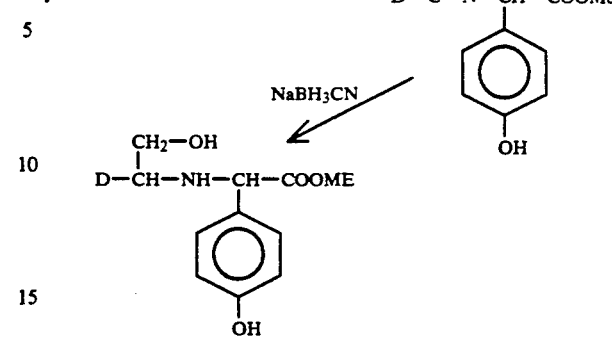

The molecule is then iodinated with iodine-123. The alternative consists in reacting 3-iodotyrosine methyl ester with Dox and performing "cold" iodine/I* exchange.

III) From the 9-carboxylanthracycline.

This synthetic route is also possible. In effect, it is necessary to use Dox as the starting material, which must be provisionally protected with a trifluoroacetyl group and then, after oxidation and reaction with 3-iodotyrosine methyl ester or tyrosine methyl ester, the protective trifluoroacetyl group must be removed before being made radioactive. The Dox derivative is protected on its terminal $NH_2$ with an N-trifluoroacetyl group. The N-trifluoroacetyl-dox is then oxidized with periodate to give the 9-carboxyl derivative, which may be activated and coupled with 3-iodotyrosine methyl ester. The trifluoroacetyl group is then removed and the derivative would be succinylated.

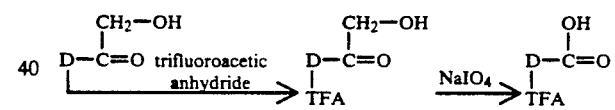

The formation of the 9-carboxyl derivative of dox by the oxidation of dox with periodate has been described by TONG et al. (J. Med. Chem. 19 (1976), 395–398).

In a second stage, the activation of the 9-carboxyl derivative is carried out, for example, with N-hydroxysuccinimide in the presence of isobutyl chloroformate, or by any other method which is traditional in peptide synthesis chemistry, and the activated derivative is reacted with 3-iodotyrosine methyl ester or tyrosine methyl ester.

In a third stage, the deprotection of the amine group is performed.

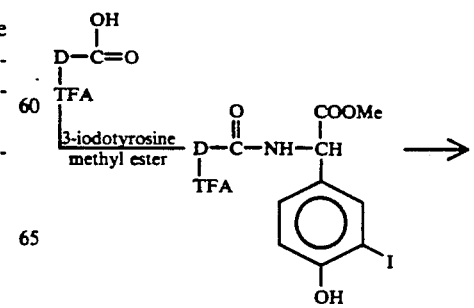

-continued $$D-\overset{O}{\overset{\|}{C}}-NH-\overset{COOMe}{\underset{}{CH}}-\underset{OH}{\underset{}{\bigcirc}}-I$$

In a fourth stage, either labeling with iodine I* or "cold" iodine/I* exchange is performed.

IV) From daunorubicin (DNR) derivatives, by GRIGNARD reaction.

The reaction of the lithium enolate of N-trifluoroacetyldaunorubicin with benzyl bromide leads to a mono- and dialkyl mixture (Smith et al., J. Med. Chem. 22 (1979) 40–44). Only the monoalkyl derivative can be deprotected with NaOH, and hence only the monoalkyl derivative can be coupled subsequently with a carrier.

From DNR $$D-\underset{TFA}{\overset{CH_3}{\underset{|}{C}}=O} \xrightarrow{TFA\ anhydride} D-\underset{TFA}{\overset{CH_3}{\underset{|}{C}}=O} \xrightarrow[\substack{+ \\ 2\text{-iodobenzyl} \\ bromine}]{diisopropylamine}$$

$$D-\underset{TFA}{\overset{O}{\underset{|}{C}}}-CH\begin{pmatrix}CH_2-\bigcirc-I \\ CH_2-\bigcirc-I\end{pmatrix} + D-\underset{TFA}{\overset{O}{\underset{|}{C}}}-CH_2-CH_2-\bigcirc-I$$

The monoiodo derivative is then deprotected with NaOH, before performing "cold" iodine/I* exchange. The radioactive derivative is then activated and coupled with the carrier protein.

B. SYNTHESIS OF TRIIODO DERIVATIVES

Starting with the 9-carboxyl derivative (described in A-III), it is possible to synthesize diaminated alkyl derivatives terminating in an amine group to which one of the 2 triiodobenzoic acids, activated by one of the methods common in peptide synthesis, is coupled via an amide link.

$$D-\overset{CH_2OH}{\underset{|}{C}}=O \xrightarrow{(see\ A\ III.1)} D-\underset{TFA}{\overset{OH}{\underset{|}{C}}=O}\xrightarrow{\overset{NH_2}{\underset{|}{(CH_2)_n}}}$$

$$D-\overset{O}{\underset{TFA}{\underset{|}{C}}}-NH-(CH_2)_n-NH_2$$

The 9-carboxyl derivative is activated by one of the methods common in peptide chemistry, and the diamine can have a chain length of between n=3 and n=12. This derivative then reacts either with activated 2,3,5-triiodobenzoic acid or with activated 3,4,5-triiodobenzoic acid. Deprotection of the trifluoroacetyl group is then performed with NaOH, before performing "cold" iodine/I* exchange, as follows.

$$D-\overset{O}{\underset{TFA}{\underset{|}{C}}}-NH-(CH_2)_n-NH_2 \xrightarrow{2,3,5\text{-triiodobenzoic acid}}$$

$$D-\overset{O}{\underset{TFA}{\underset{|}{C}}}-NH-(CH_2)_n-NH-\overset{O}{\overset{\|}{C}}-\underset{I}{\underset{I}{\bigcirc}}-I$$

EXAMPLE III

LIGANDS SPECIFIC FOR THE ESTROGEN RECEPTOR

Scheme I below illustrates the synthesis of a ligand 11β-chloromethyl-17α-iodovinylestradiol.

Stage 1 consists of a microbiological hydroxylation with an "ASPERGILLUS OCHRACEUS" strain at 11α according to the details provided on page 136 of reference 4. The starting substance is 17α-ethynylestradiol [1].

Stage 2 is an oxidation with pyridinium chlorochromate (PCC) in $CH_2Cl_2$, which oxidation hence provides a keto group at the 11-position according to the protocol described on page 2649 of reference 7.

Stage 3 consists of a protection with the 1-ethoxyethyl ether by the action of ethyl vinyl ether in the hydroxyl group at the $C_3$-position. The procedure to be followed is described on page 334 of reference 2.

Stage 4 consists of a methylenation of the keto group at the $C_{11}$-position by the addition of $(CH_3)_3Si\ CH_3Mg$ Cl, the details of which are described on page 39 of reference 3.

Stage 5 consists of a dehydration with an HCl/acetone mixture in accordance with the procedure detailed on page 39 of reference 3 and a deprotection of the groups at $C_3$ and $C_{17}$.

Stage 6 consists of a selective hydroboration of the double bond at $C_{11}$ with 9-borabicyclo[3.3.1]nonane BBN), the details of which are provided in reference 8.

Stage 7 consists of a hydroxylation of the BBN derivative by oxidation with sodium hydroxide (NaOH) and hydrogen peroxide ($H_2O_2$). This type of hydroxylation is described on page 334 of reference 2.

Stage 8 is a chlorination with triphenylphosphine and N-chlorosuccinimide (NCS) in accordance with the process described on page 500 of reference 5. An 11β-chloromethyl derivative is hence obtained.

Stage 9 is a hydroboration with catecholborane at 70° C. for 2 hours according to the process described on page 1289 of reference 6. A 17α-vinyl derivative is hence obtained.

Stage 10 is a formation of an acetate derivative at the $C_3$-position with acetic anhydride and pyridine. This type of process is described on page 1289 of reference 6.

Stage 11 is an iodination stage according to the method of NAKATSUKA (page 1289 of reference 6), with chloramine T, NaI*, THF and a phosphate buffer. A 17α-iodovinyl derivative is obtained.

Stage 12 is a deprotection of the group at the $C_3$-position by hydrolysis of the acetate group with sodium acetate and $Na_2CO_3$ in methanol, and ether (according to the details supplied on page 1289 of reference 6). 11β-Chloromethyl-17α-iodovinylestradiol ($I^{125}$ or $I^{123}$) [2] is thereby obtained.

Another access route to the intermediate [3] obtained at the end of stage 8 is the aromatization of the intermediate [5] resulting from stage 8 during the synthesis route in Scheme II of the following example. The aromatization of the intermediate [5] taking place after acid deprotection of its ethylene dioxide group at the $C_3$-position. This aromatization is carried out microbiologically with the "ARTHROBACTER SIMPLEX" strain (this process is carried out according to that described in reference 1). The yield and the purity of the intermediate [5] during the chlorination stage being relatively better than those which can be obtained during the synthesis of [3].

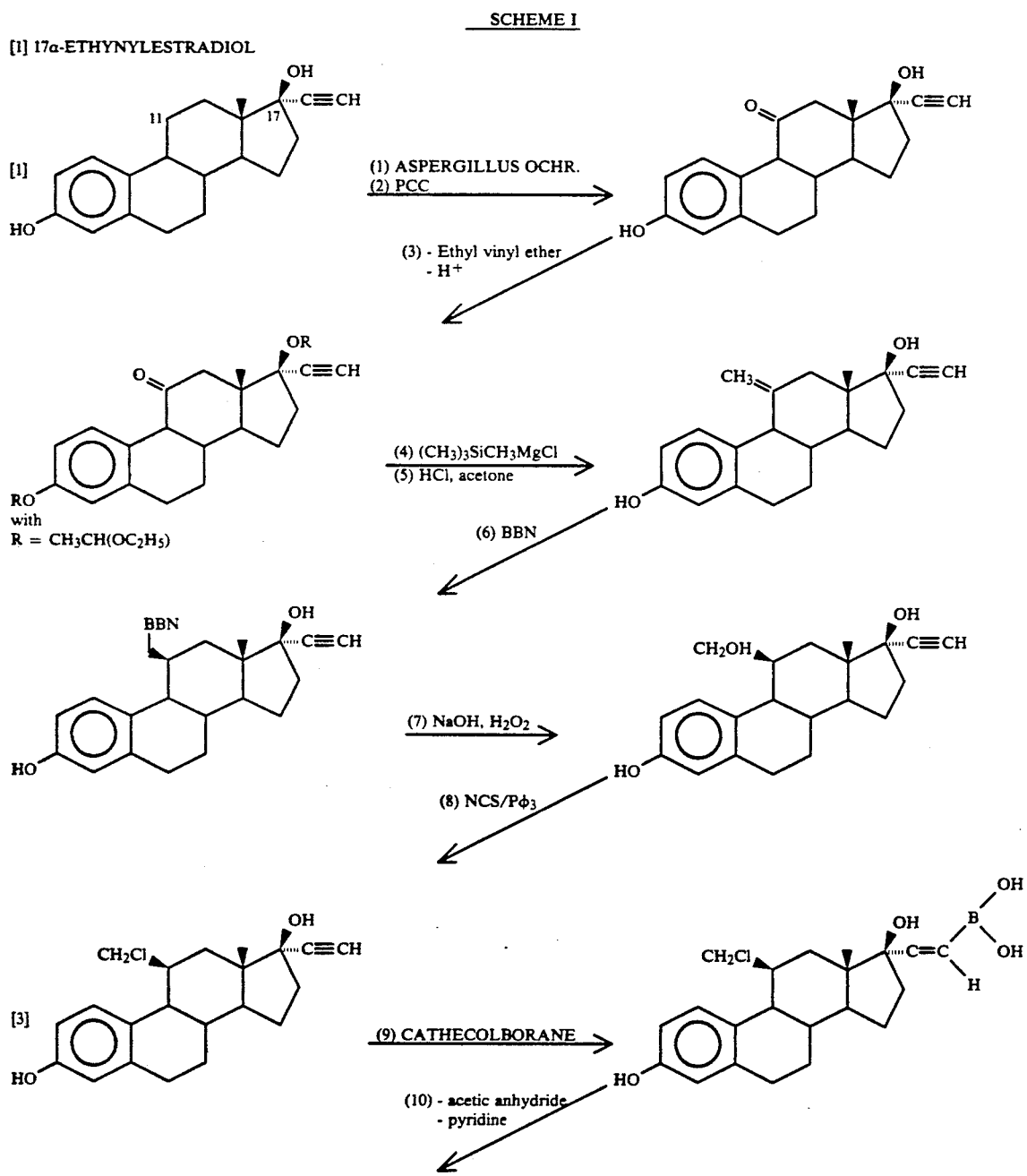

-continued
SCHEME I

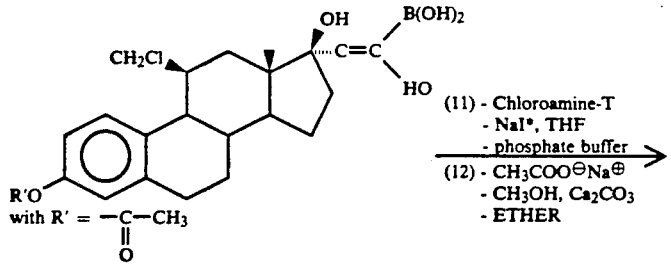
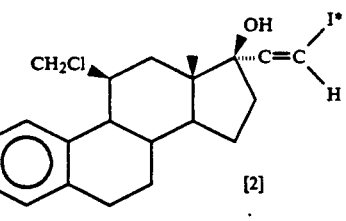

[2] = 11β-CHLOROMETHYL-17α-IODOVINYLESTRADIOL

B - Scheme Ia below illustrates a novel synthesis of the ligand 11β-chloromethyl-17α-iodovinylestradiol.

Stage 1 consists of a preparation of Δ¹-adrenosterone 17-(ethylene acetal) from Δ¹-adrenosterone (1').

25 g of Δ¹-adrenosterone (84 mM) are added with vigorous stirring to a mixture of 500 ml of benzene, 25 ml of ethylene glycol (approximately 420 mM) and 1 g of para-toluenesulfonic acid.

The mixture is brought to reflux for 4 hours in a Dean and Stark apparatus.

The reaction mixture is extracted with 200 ml of water containing 1 g of bicarbonate, and then with water saturated with salt, dried and then evaporated.

A yellowish mass is obtained, which is washed in the hot state with 200 ml of isopropyl ether.

The white crystals are filtered off and then dried at 60° C., and a mass of ±26 g is obtained.

Stage 2 consists of the preparation of 11β-hydroxy-1,4-androstadiene-3,17-dione 17-(ethylene acetal) (2').

340 g of (1') (88 mM) are added under nitrogen to a suspension of 50 g (±200 mM) (lacuna) in 400 ml of tetrahydrofuran.

After 24 hours' reaction at room temperature, 100 ml of ether are added, followed by 40 ml of 1N NaOH and then 25 g of anhydrous sodium sulfate. Stirring is maintained overnight.

The mixture is filtered and the filtrate is then evaporated under vacuum.

The solid mass obtained is washed in the hot state with 200 ml of diisopropyl ether.

After filtration and drying, 24 g of a white powder (70.6 mM) are obtained.

Stage 3 consists of the preparation of 3,11β-dihydroxy-1,3,5(10)-estratrien-17-one 17-(ethylene acetal) (3').

A mixture of 3 g of lithium coated in oil (approximately 0.4 M), 25 g of biphenyl (0.16 M (sic)) and diphenylmethane (0.08 M) in 360 ml of tetrahydrofuran is brought to reflux for 1 hour under a nitrogen atmosphere.

The dark blue reaction mixture, to which 20.7 g of (2') are added, is again brought to reflux for 30 minutes.

After the mixture is cooled, 8 ml of methane are added, followed by 100 ml of water, and the solvent is evaporated off under vacuum.

After redissolution in the remaining mass in ether, the product formed is extracted with 300 ml of 5% KOH, which is reacidified with acetic acid (12 ml).

The yellow precipitate is re-extracted with ethyl acetate. After evaporation of the solvent, the product is redissolved in the hot state in 15 ml of a mixture of acetone and diisopropyl ether.

After two crystallizations, 10.5 g of product are obtained.

The corrected melting point is: 191.1° C.

Stage 4 consists of the preparation of 3-benzyloxy-11β-hydroxy-1,3,5(10)-estratrien-17-one 17-(ethylene acetal) (4').

A mixture of 10.3 g of (3') (30 mM), 5.2 g of ground anhydrous K₂CO₃ and 100 ml of methyl ethyl ketone is brought to reflux with vigorous stirring for 1 hour.

5.4 ml (45 mM) of benzyl bromide are then added and refluxing is maintained for 48 hours.

After extraction, 15 g of yellowish oil are obtained.

This oil is employed as it is in the synthesis of (5').

Stage 5 consists of the preparation of 3-benzyloxy-1,3,5(10)-estratriene-11,17-one 17-(ethylene acetal) (5').

30 mM of crude (4') (13 g) dissolved in 50 ml of dry methylene chloride are added in a single portion to a mixture of 13 g of pyridinium chlorochromate suspended in 200 ml of dry methylene chloride.

After 3 hours' stirring at room temperature, 250 ml of ether are added, thereby causing the precipitation of a black mass.

The solvents are decanted and the insoluble material is washed with 4 times 50 ml of a v/v $CH_2Cl_2$/ether mixture.

The organic phase is percolated through a column of florisa and then evaporated.

After purification of silica, 9.6 g of a yellowish oil are obtained.

Stage 6 is the preparation of 3-benzyloxy-11-hydroxy-11-methyltrimethylsilane-1,3,5(10)-estratrien-17-one 17-acetal (6').

8.6 g of (5'), dissolved in 100 ml of ether (20 mM) are added rapidly to 165 ml of a 1 M solution of methyltrimethylsilanemagnesium chloride.

The mixture is brought to reflux for 5 hours, and then decomposed and extracted.

The crude product is purified on silica, and 5.7 g of a viscous oil which crystallizes are obtained.

Stage 7 is the preparation of 3-benzyloxy-11methylene-1,3,5(10)-estratrien-17-one (7').

After the addition of 0.5 ml of concentrated HCL, a solution of 5.2 g of (6') (10 mM) in 50 ml of acetone is stirred for 2 hours at room temperature. The reaction mixture is neutralized with concentrated HCO₃ under vacuum, and extracted with $CH_2Cl_2$.

The crude product is recrystallized in acetone. 3.4 g of yellowish crystals are obtained.

The corrected melting point is 168.1° C.

Stage 8 consists of the preparation of 3-benzyloxy-11-methylene-1,3,5(10)-estratrien-17-one 17-acetal (8').

A solution of 3 g of (7'), 7 mM, 100 ml of benzene, 3 ml of diethylene glycol and 150 mg of paratoluenesulfonic acid is refluxed in a Dean and Stark apparatus for 4 hours.

Extraction, followed by evaporation of the solvents, gives 3.3 g of a white oil which is employed as it is.

Stage 9 consists of the preparation of 3-benzyloxy-11-hydroxymethyl-1,3,5(10)-estratrien-17-one 17-acetal (9').

A solution of 2.84 g of (8') (±6 mM) in 20 ml of dry THF is treated with 0.5 ml of borane/oxathione complex (±6 mM). After 1 hour's reaction, 6 ml of ethanol are added, followed by 4 ml of 3 M NaOH (±12 mM) and finally 10 ml of 30% $H_2O_2$ (±12 mM (sic)). After one night at room temperature, the reaction mixture is extracted with $CH_2Cl_2$. A white oil is obtained, which crystallizes rapidly (weight: 2.4 g).

Stage 10 consists of the preparation of 3-benzyloxy-11-chloromethyl-1,3,5(10)-estratrien-17-one (10').

The suspension formed in 30 ml of THF by the reaction of 2.1 g of triphenylphosphine (8 mM) and 1.07 g (±8 mM) of N-chlorosuccinimide is added to a solution of 2 g of (9'), approximately 4 mM, in 20 ml of tetrahydrofuran.

The mixture, which has become clear after about 1 hour, is left at room temperature overnight. The THF is evaporated off under vacuum, and the crude residue is redissolved in 50 ml of acetone, to which 0.5 ml of concentrated HCl is added. The mixture is left with stirring for 2 hours. Extraction, followed by purification on silica, gives white crystals amounting to 1.02 g.

MS (FAB) 435 (M+1).

Stage 11 consists of the preparation of 3-benzyloxy-11-chloromethyl-17α-ethynyl-17β-hydroxy-1,3,5(10)estratriene (11').

400 mg (±4 mM) of ethylenediamine/lithium acetylide complex are added to a solution of 0.93 g of (10') (about 2 mM) in 10 ml of tetrahydrofuran. After 4 hours' reaction, 400 mg of reagent are added again. The mixture is left to react overnight at room temperature.

Extraction with $CH_2Cl_2$, followed by purification on silica, yields a slightly yellowish solid weighing approximately 500 mg (1.02 mM).

Stage 12 consists of the preparation of 11-chloromethyl-3,17β-dihydroxy-17α-ethynyl-1,3,5(10)estratriene (12').

440 mg of (11'), 0.9 mM), are dissolved in the cold state in 20 ml of methylene chloride.

4.5 ml (4.5 mM) of a 1 M solution of BF3/ (CH3)2S are then added.

The reaction mixture is stirred in the cold state for 45 minutes.

Extraction, followed by purification on silica, yields an oil which crystallizes with a mass of approximately 150 mg (0.375 mM).

Stage 13 consists of the preparation of the derivative (E)-11-chloromethyl-3,17β-dihydroxy-17α-(2-tributylstannylvinyl)-1,3,5(10)-estratriene (13').

150 μl of tributyltin hydride (about 0.55 mM) and 5 mg of AIBN (about 0.03 mM) are added under $N_2$ to a solution of 50 mg of (12'), 0.15 mM), in 1 ml of THF.

The tube is hermetically sealed and then stirred on an oil bath at 70° C. for 1 hour.

The reaction mixture is extracted with an ethyl acetate/water mixture

The crude oil is purified with silica; 55 mg of a white oil are obtained.

Stage 14 consists of the preparation of the derivative (E)-11-chloromethyl-3,17β-dihydroxy-17α-(2-iodovinyl)--1,3,5(10)-estratriene (14').

A 0.1 mM solution of iodine in $CH_2Cl_2$ is added dropwise to a solution of 32 mg of (13') (0.05 mM) in 3 ml of $CH_2Cl_2$ until the pinkish coloration persists.

After 30 minutes, about 10 ml of $H_2O$ with a little $NaHSO_3$ are added, and the mixture is extracted with $Et_2O$.

The crude product is then purified on silica; 20 g of white crystals are obtained having a mass of 20 mg.

Spectroscopic data: NMR ($CDcl_3$, $(CD_3)_2SO$) S 1.1 (S,13CH3), 3.45 (m,CHHcl), 3.62 (dd, CHHcl), 6.27 (d, CH=CHI, J=14 Hz), 6.53 (d, H(4)), 6.66 (dd, H(2)), 6.81 (d, CH=CHI, J=14 Hz), 7.03 (d, H(1)).

LABELING USING THE TRIBUTYLTIN DERIVATIVE

50 μl of a solution of the derivative (E)-17α-tributylstannylvinyl-11β-chloromethylestradiol (13' of Scheme 1a) in absolute ethanol at a concentration of 1 mg/ml are added to 1 mCi of $NaI^{123}$ (10μl in $H_2O$ pH 7-11) contained in an approximately 500 μl screw-capped tube. 10 μl of a solution of chloramine T at a concentration of 1 mg/ml are added and the mixture is agitated vigorously for 15 seconds. 10 μl of a solution of $Ha_2S_2O_5$ at a concentration of 2 mg/ml and 200 μl of phosphate buffer, pH 7.4, are then added. The mixture is passed through an SPE C18 cartridge (1 ML, BAKER) and the steroid is eluted with 1 ml of ethanol. After evaporation of the solvent, the labeled steroid is purified on a μ BONDAPAK C18 HPLC column with a 50% $H_2O$ and 50% acetonitrile mobile phase. The retention time is of the order of 17 minutes.

SCHEME 1a

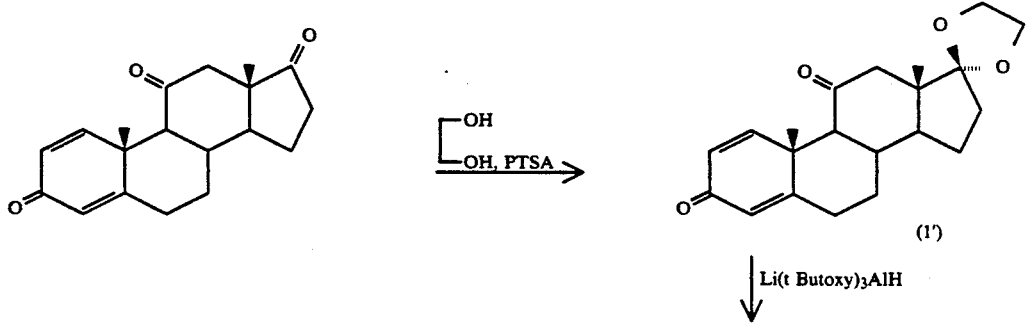

-continued
SCHEME 1a
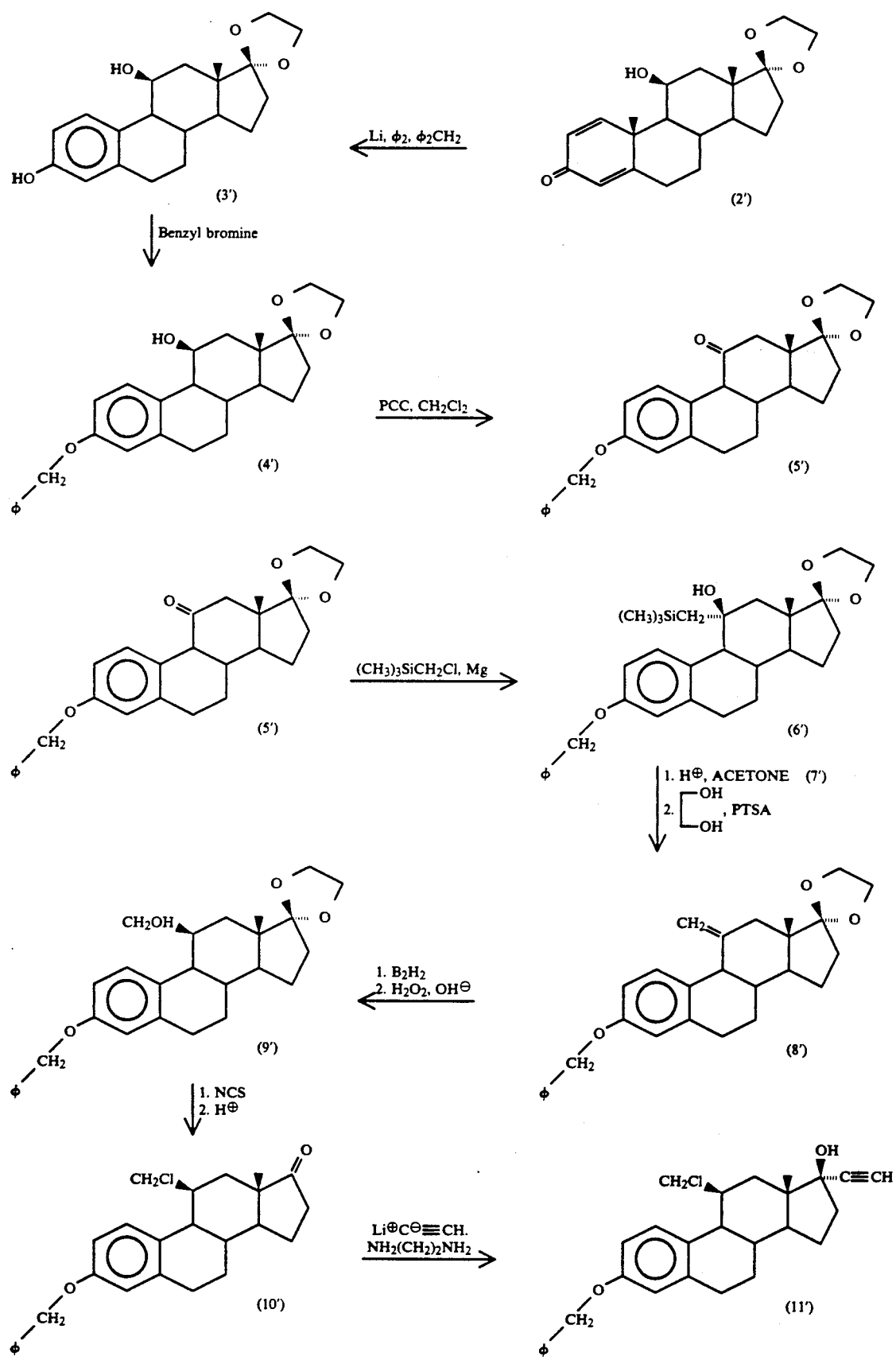

-continued
SCHEME 1a

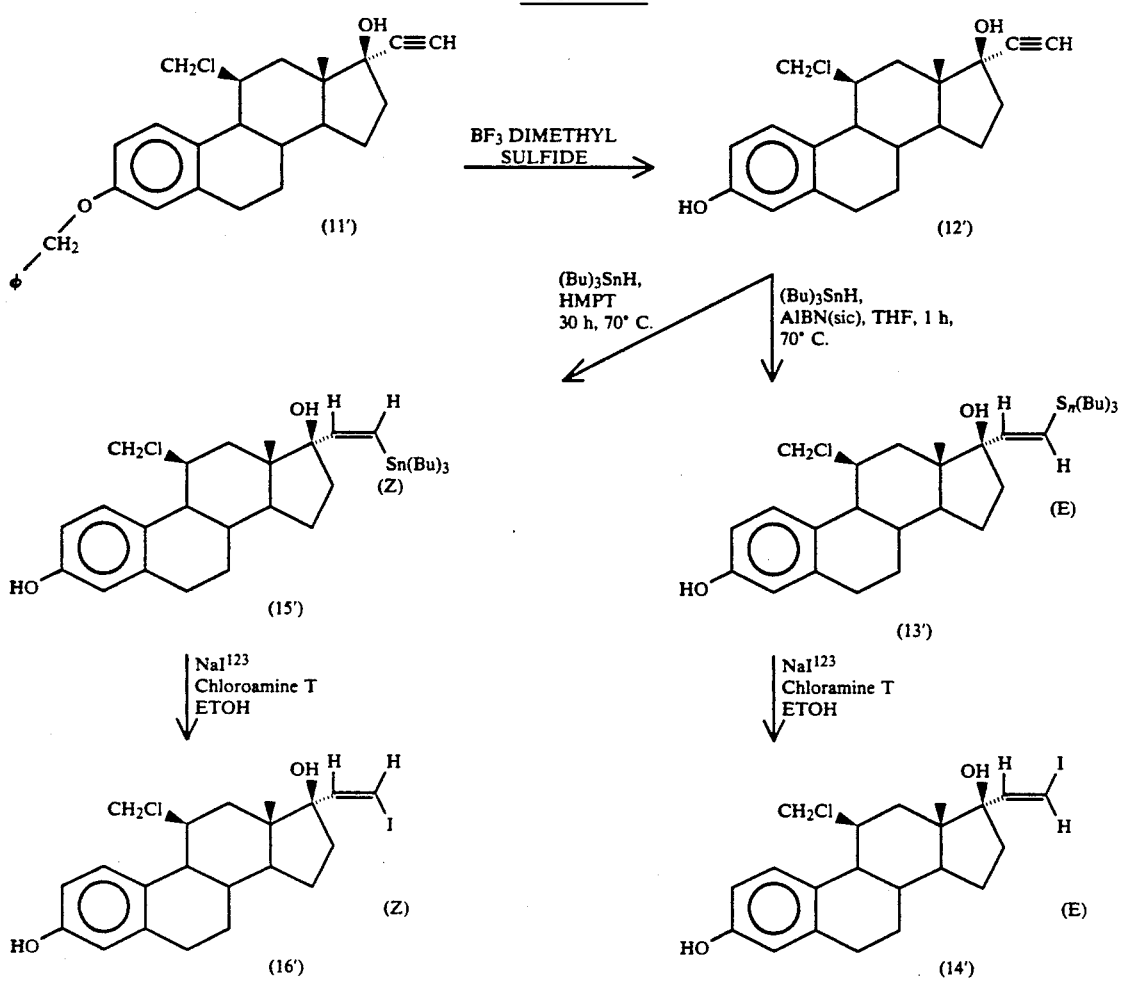

EXAMPLE IV

LIGANDS SPECIFIC FOR THE PROGESTAGEN RECEPTOR

The synthetic route for 11β-chloromethyl-17α-iodovinyl-17β-hydroxy-19-nor-4-androsten-3-one derivatives is described with reference to Scheme II below.

The starting substance is 17α-ethynyl-17β-hydroxy-19-nor-4-androsten-3-one (NORETHINDRONE) [4].

In this scheme, I* denotes the isotopes $I^{125}$ or $I^{123}$.

Stage 1 is a stage of protection of the keto group at $C_3$ with an ethylenedioxy group. For this purpose, ethylene glycol, p-toluenesulfonic acid and ethyl orthoformate and $CH_2Cl_2$ as solvent are used (details of this type of process are supplied on page 39 of reference 3).

Stage 2 is a stage of protection of the hydroxyl group at the 17α-position, protection being with a 1-ethoxyethyl ether group (according to stage 3 of Scheme I of Example I).

Stage 3 is a stage of microbiological hydroxylation at 11α according to the process of stage 1 of Scheme I.

Stage 4 is an oxidation stage with pyridinium chlorochromate (PCC) in the neutral state by buffering with sodium acetate according to a type of process described (synthesis of CITRONELLAL, page 2649 of reference 7). A keto group at the $C_{11}$-position is thereby obtained.

Stage 5 consists of a methylenation of the $C_{11}$-position by a WITTIG reaction, using methyltriphenylphosphonium bromide and NaH in DMSO, in accordance with the process described on page 39 of reference 3.

Stages 6, 7 and 8 resemble stages 6, 7 and 8 of Scheme I. The same applies to stages 9 and 10, which resemble stages 9 and 11, respectively, of Scheme I.

Stage 11 of the present process consists of a deprotection with HCl in acetone, in accordance with the procedure described on page 334 of reference 2, to give the compound [6], 11β-chloromethyl-17α-iodovinyl-17β-hydroxy-19-nor-4-androsten-3-one.

SCHEME II
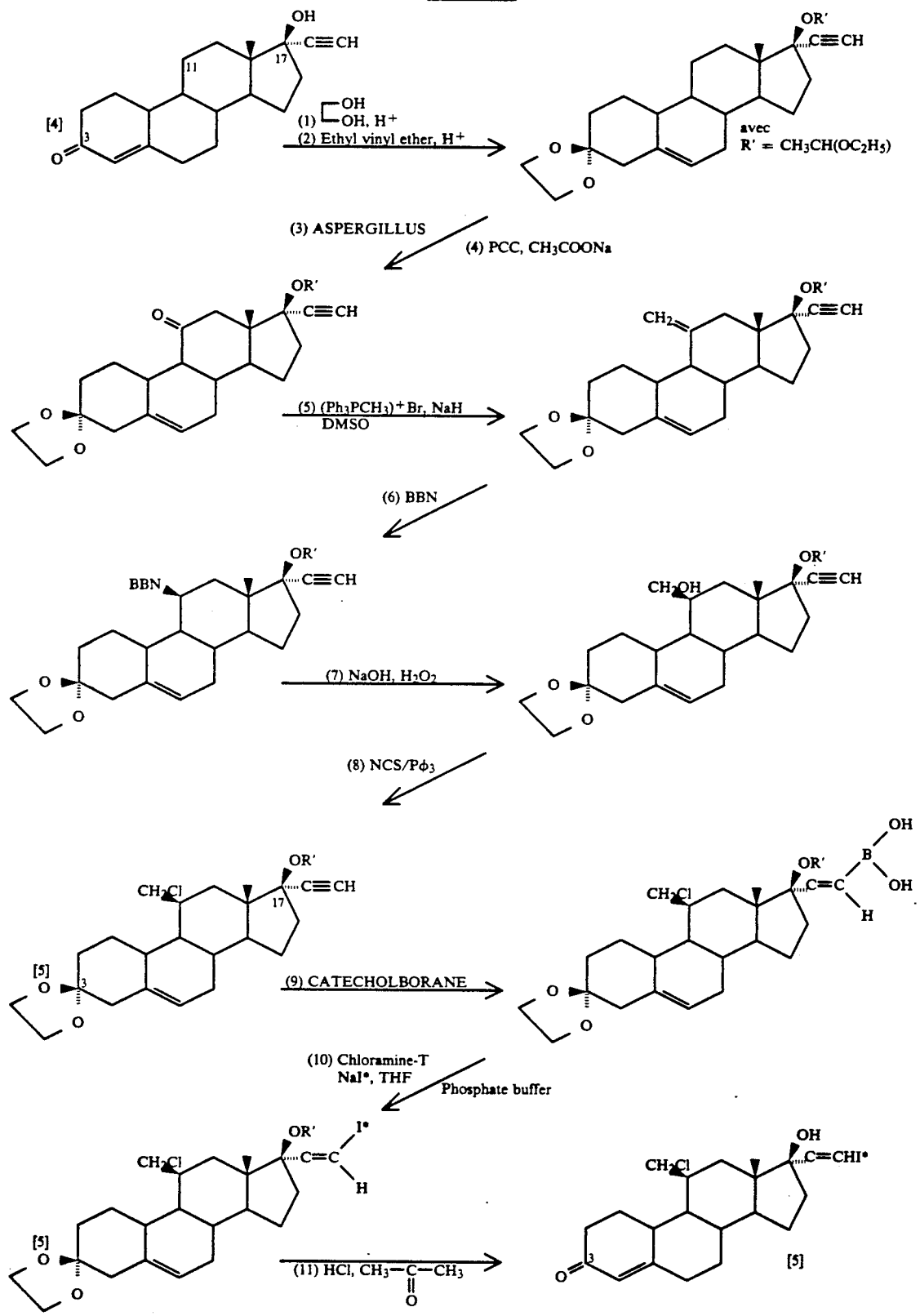

EXAMPLE V

LIGANDS SPECIFIC FOR THE ANDROGEN RECEPTOR

The synthetic route for an 11β-chloromethyl-17α-methyl-18-iodotestosterone derivative [8] is shown in Scheme III below.

The starting substance is an 11α-hydroxy-17α-methyltestosterone derivative [7].

Stage 1 is a stage of protection, resembling that of stage 1 of Scheme II, by ethylene glycol in an acid medium.

Stage 2 is an oxidation stage, (lacuna) stage 4 of Scheme II, by pyridinium chlorochromate in the neutral state with a sodium acetate buffer Stage 3 is a stage of protection resembling stage of Scheme I.

Stage 4 is a stage of addition of a methyl at the $C_{11}$-position by the action of $CH_3Li$ in a benzene/diethyl ether mixture in accordance with the details supplied on page 39 of reference 3.

Stage 5 is a dehydration resembling stage 5 of Scheme I.

Stage 6 is a hydroboration with BBN, as in stage of Scheme I.

Stage 7 is a hydroxylation like that of stage 7 of Scheme I.

Stage 8 is a chlorination resembling stage 8 of Scheme I with NCS/Pφ3. An 11β-chloromethyl product [11] is thereby obtained.

Stage 9 is an iodination of methyl at the 18-position, by the prior action of lead tetraacetate and radioactive iodine under reflux in cyclohexane, followed by addition of the steroid [11] and azodisobutyronitrile according to the process described in page 506 of reference 5. 11β-Chloromethyl-17α-methyl-18-iodotestosterone [8] is thereby obtained.

The analogous derivatives [10] and [9] are formed from the product of microbiological hydroxylation, as in stage 1, of the derivative 17α-methyl-19-nortestosterone and of mibolerone (7α, 17α-dimethyl-19-nortestosterone), respectively, and undergo the same stages from 4 to 9 of the present scheme. Mibolerone and 17α-methyl-19-nortestosterone have a better affinity than testosterone for the androgen receptor.

In addition, mibolerone described in U.S. Pat. No. 3,341,557 has a smaller affinity than testosterone for the plasma binding proteins, and a markedly higher nuclear retention endows the derivative [9] with a targeting of high specificity.

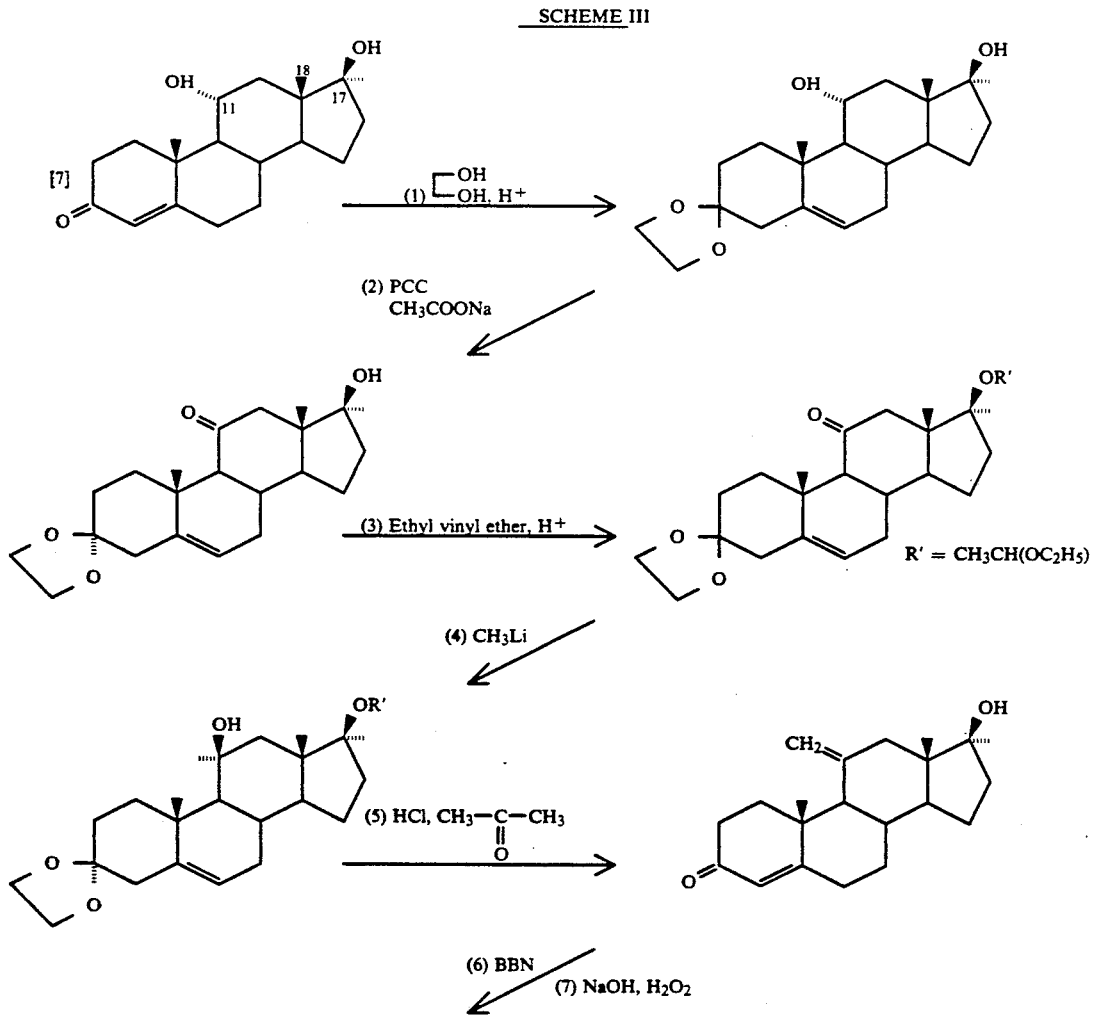

SCHEME III

-continued
SCHEME III

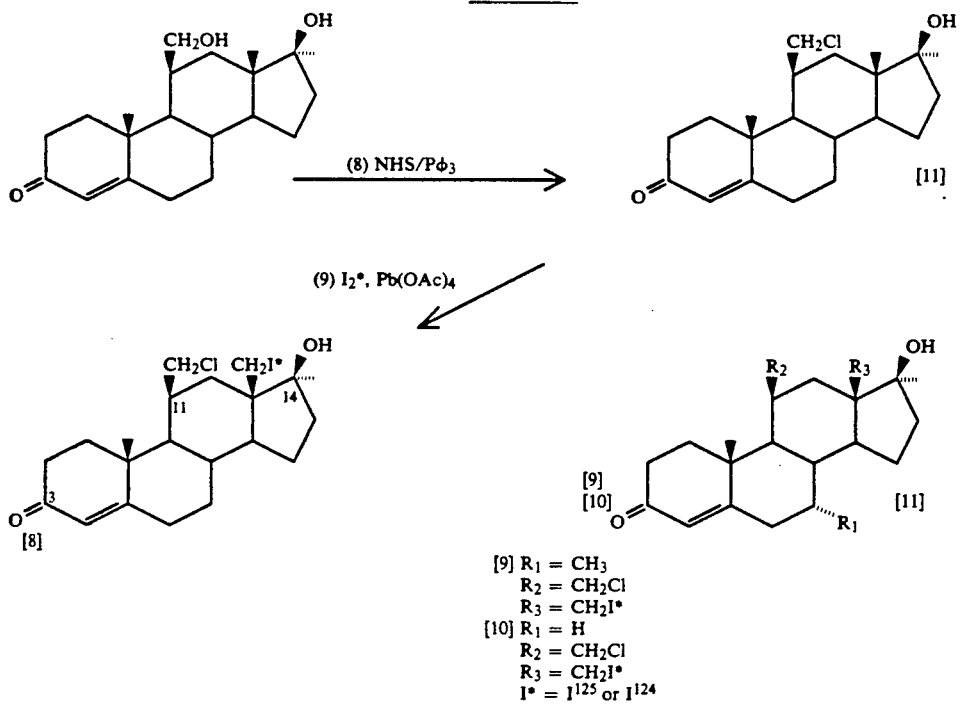

[9] R₁ = CH₃
    R₂ = CH₂Cl
    R₃ = CH₂I*
[10] R₁ = H
     R₂ = CH₂Cl
     R₃ = CH₂I*
I* = I¹²⁵ or I¹²⁴

EXAMPLE VI

Inhibition of the growth of malignant cells by 17beta-iodovinylestradiol (I$^{125}$ and I$^{123}$).

The labeling of the steroid was carried out according to the protocol described in Journal of Nuclear Medicine Vol. 23 No. 5 pages 431 to 436, 1982 Robert N. HANSON et al.

The measurement of the inhibition of the growth of malignant cells was carried out following the protocol described by MADEDDU et al. in ANTICANCER RESEARCH 6: 11-16(1986).

The inhibition of the growth of MCF7 cells (human mammary carcinoma continuous line containing receptors for estrogens) and EP2 cells (pharyngeal epithelioma continuous line not possessing receptors for estrogens was measured on the fifth day, the inhibition being by I$^{125}$- or I$^{123}$-labeled 17beta-iodovinylestradiol. It is found that this ligand 17beta-iodovinylestradiol labeled with iodine-123 (one molecule of iodine for one molecule of ligand), at a concentration of 4.6×10$^{-10}$ M corresponding to 31.3 μCi/ml, gives percentage growth values for MCF7 cells (5000 cells per well for the control) of 56.2%, equivalent to an inhibition of growth of 43.8%, and for EP2 cells (control 5000 cells per well) a growth of 97%, equivalent to an inhibition of only 3%.

The same ligand containing an iodine-125 at the same concentration of 4.6×10$^{-10}$ M, corresponding to 1 μCi/ml, gave an inhibition of only 10.4% for MCF7 cells (control 5000 cells per well), and for EP2 cells, the percentage growth was 105.1%.

Accordingly, the compound labeled with iodine-123 exhibits a very advantageous inhibition of growth with respect to MCF7 cells.

REFERENCES (1) A. J. VAN DEN BROEK et al., PHARMACEUTISCH WEEKBLAD SC. ED., p. 182-183, Vol. 5, 1983, (2) K. H. SCHONEMANN et al., EUR. J. MED. CHEM. CHIMICA THERAP. - p. 333-335, 15 No. 4, 1980

(3) A. J. VAN DEN BROEK et al., RECUEIL JOURNAL OF THE ROYAL NETHERLANDS CHEMICAL SOC. - p. 35-39, 94/2, 1975, (4) J. DE FLINES et al., RECUEIL J. ROYAL NETH. CHEM. SOC. p. 129) 138, 82, 1963, (5) A. J. VAN DEN BROEK et al., STEROIDS - p. 481-510, 30, 1977, (6) I. NAKATSUKA et al., J. OF MEDICINAL CHEMISTRY, p. 1287-1291, 27, No. 10, 1984, (7) E. J. COREY and W. SUGGS, TETRAHEDRON LETTERS, p. 2647-2650, No. 31, 1975, (8) C. A. BROWN and R. A. COLLMAN, J. ORG. CH., P 2328, 44, 1979.

We claim:

1. A ligand specific for steroid hormone receptors which is useful for targeted therapy or imaging of cancer, comprising a parent structural skeleton of the formula:

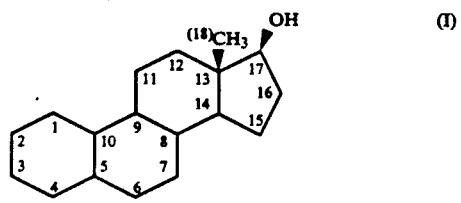

(I)

and wherein said ligand further comprises:
a hydroxyl or keto group at the C₃-position, a β-oriented chloromethyl group on the $C_{11}$-position, an α-oriented vinyl or methyl group on the $C_{17}$-position, and a radioactive iodine substituted on an alkyl or alkenyl group attached to the skeleton.

2. The ligand of claim 1, wherein said alkyl or alkenyl group is a methyl or a vinyl group.

3. The ligand of claim 1, wherein said ligand is used in targeted therapy and the radioactive iodine is the isotope $I^{125}$ or $I^{123}$.

4. The ligand as claimed in claim 3 in which the radioactive iodine is situated on a double bond of an α-oriented vinyl on the $C_{17}$ position.

5. The ligand as claimed in claim 3 in which the radioactive iodine is situated on an angular methyl at position $C_{18}$.

6. The ligand of claim 1, wherein said ligand is used in imaging and the radioactive iodine is the isotope $I^{123}$.

7. The ligand as claimed in claim 6, in which the radioactive iodine is situated on a double bond of an α-oriented vinyl on the $C_{17}$ position.

8. The ligand as claimed in claim 6 in which the radioactive iodine is situated on an angular methyl at position $C_{18}$.

9. The ligand of claim 1, wherein said radioactive iodine is situated on a double bond of an α-oriented vinyl or methyl group on the $C_{17}$-position.

10. The ligand as claimed in claim 9, in which the group at the $C_3$-position is a hydroxyl group attached to an aromatic ring.

11. The ligand of claim 10, wherein said ligand is an 11β-chloromethyl-17α-iodovinylestradiol of the formula

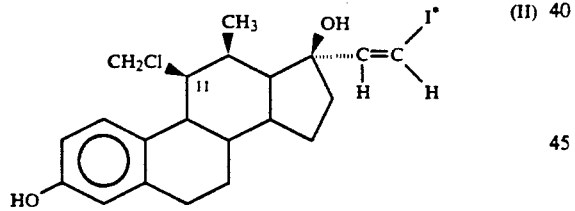

(II)

12. The ligand as claimed in claim 9, in which the group at the $C_3$-position is a keto group conjugated with a $C_4$-$C_5$ double bond.

13. The ligand of claim 12, wherein said ligand is an 11β-chloromethyl-17α-iodovinyl-17β-hydroxy-19-nor-4-androsten-3-one of the formula

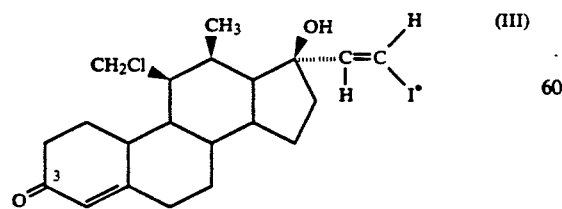

(III)

14. The ligand of claim 1, wherein said radioactive iodine is situated on an angular methyl group positioned at $C_{18}$.

15. The ligand as claimed in claim 14, in which the group at the $C_3$-position is a keto group conjugated with a $C_4$-$C_5$ double bond.

16. The ligand of claim 15, wherein said ligand comprises a methyl group positioned at $C_7$.

17. The ligand of claim 15, wherein said ligand is an 11β-chloromethyl-17α-methyl-18-iodotestosterone of the formula

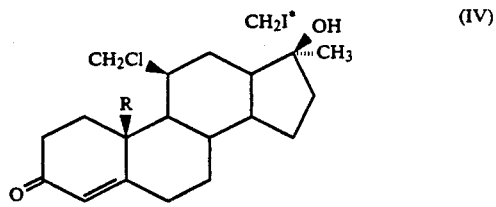

(IV)

and wherein $R = CH_3$.

18. The ligand of claim 15, wherein said ligand is 11β-chloromethyl-17α-methyl-18-iodo-7α-methyl-19-testosterone of the formula

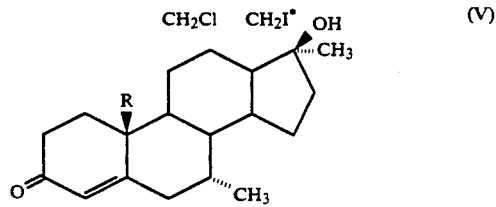

(V)

and wherein $R = CH_3$.

19. The ligand of claim 15, wherein said ligand is an 11β-chloromethyl-17α-methyl-19-nortestosterone of the formula

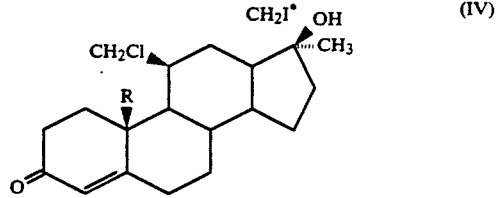

(IV)

and wherein $R = H$.

20. The ligand of claim 15, wherein said ligand is an 11β-chloromethyl-17α-methyl-18-iodo-7α-methyl-19-nortestosterone of the formula

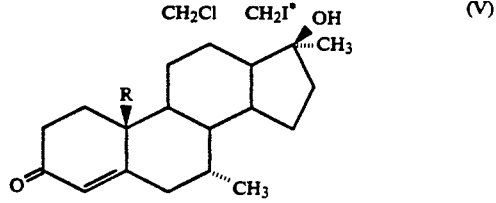

(V)

and wherein $R = H$.

* * * * *

UNITED STATES PATENT AND TRADEMARK OFFICE
CERTIFICATE OF CORRECTION

PATENT NO. : 5,096,694

DATED : March 17, 1992

INVENTOR(S) : Jacques Quivy et al.

It is certified that error appears in the above-identified patent and that said Letters Patent is hereby corrected as shown below:

On the title page: Item [22]  change "Apr. 19, 1988" to --Apr. 15, 1988--.

Signed and Sealed this

Fifth Day of October, 1993

*Attest:*

BRUCE LEHMAN

*Attesting Officer*  Commissioner of Patents and Trademarks